United States Patent [19]

Arpesella

[11] Patent Number: 4,561,129
[45] Date of Patent: Dec. 31, 1985

[54] LOW-PROFILE BIOLOGICAL BICUSPID VALVE

[75] Inventor: Marco Arpesella, Rimini, Italy

[73] Assignee: Pro. Bio. Spe. S.r.l., Rimini, Italy

[21] Appl. No.: 540,896

[22] Filed: Oct. 11, 1983

[30] Foreign Application Priority Data

Oct. 14, 1982 [IT] Italy ................................ 3559 A/82

[51] Int. Cl.$^4$ .............................................. A61F 1/22
[52] U.S. Cl. ...................................................... 623/2
[58] Field of Search ............................................. 3/1.5

[56] References Cited

U.S. PATENT DOCUMENTS

| | | | |
|---|---|---|---|
| 3,312,237 | 4/1967 | Mon et al. | 3/1.5 X |
| 3,739,402 | 6/1973 | Cooley et al. | 3/1.5 |
| 3,859,668 | 1/1975 | Anderson | 3/1.5 |
| 3,983,581 | 10/1976 | Angell et al. | 3/1.5 |
| 4,218,782 | 10/1980 | Rygg | 3/1.5 |
| 4,308,624 | 1/1982 | Klawitter | 3/1.5 |

FOREIGN PATENT DOCUMENTS

EP002931 7/1979 European Pat. Off. ................ 3/1.5

OTHER PUBLICATIONS

"A Hinged-Leaflet Valve for Total Replacement of the Human Aortic Valve", by V. L. Gott et al., Journal of Thoracic & Cardiovascular Surgery, vol. 48, No. 5, Nov. 1964, pp. 713-725.

Primary Examiner—Ronald L. Frinks
Attorney, Agent, or Firm—Collard, Roe & Galgano

[57] ABSTRACT

This invention relates to a "biological" valve suitable for surgical treatment of cardiopathies, composed of a supporting ring having a diametrically-disposed element which functions as a support for the hinge of the two flaps which alternately allow and prevent flow through the device. It is designed in such a way that the angle formed by these flaps in the resting position conditions both the height of the prosthesis as well as the mechanical behavior of the aforementioned flaps.

14 Claims, 9 Drawing Figures

LOW-PROFILE BIOLOGICAL BICUSPID VALVE

The present invention relates to a "biological" valve suitable for use as a cardiac valve prosthesis in the surgical treatment of various cardiopathies.

Presently, only two types of such "biological" valves are available: those with three cusps obtained from the aortic valves of pigs, preserved in glutaraldehyde and mounted on a fixed support; and those obtained from bovine pericardium (also preserved in glutaraldehyde) and cut and assembled in such a way as to produce a valve with three cusps. Both types of valves cause certain problems; for example, the porcine valves, being obstructed by the muscular part above one of the cusps, have a smaller useful area of inflow, while those made from bovine pericardium, being made of a protruding high-profile support ring, present the risk of ventricular lesions. Additionally, both valve types exhibit problems linked to the presence of high transprosthethic gradients (i.e., a reduction in the effective size of the opening with respect to that of the actual cardiac implant).

It is therefore an object of the present invention to eliminate the above-mentioned problems and to provide a device which allows an improvement in hemodynamic performance, thus achieving a greater, useful area for flow and lower transprosthetic gradients.

It is a more particular object of the invention to provide such an improved valve bioprosthesis having a low profile.

These and other objects are achieved by a device according to the invention, which has a central element or support supporting two movable flaps which serve as valve cusps. The central element is preferably supported by a round or oval ring-like element, stent or frame which is mounted on the crown or rim for the cardiac implant. Further adaptation of the ring can be obtained by simply straightening the two arches subtended by the four lower insertion points of the moving flaps (as will be described and illustrated hereinafter).

The frame which exhibits an appropriate belling or scalloping is provided on its outer surface with joint means or holes in order to permit it to be integrally joined to the crown for the implant (e.g., the holes would allow the passage of sutures for fixing the implant to the myocardium. The central element is attached to this frame and completes the rigid structure of the prosthesis. In a first embodiment, the central element consists of an arched or straight rib positioned diametrically to the ring and integrally joined thereto. In a second embodiment the rib is replaced by a double-arched, sawhorse-like structure.

The rigid support structure of the device is provided with a covering and, if the covering chosen requires it, the support elements are provided with grooves or holes to facilitate anchoring of the covering. In particular, the support frame or ring can be covered with preserved pericardium, Dacron (i.e., a polyester fiber), Teflon (polytetrafluoroethylene), and other biocompatible materials by means of suturing, fusing together, adhesion and other methods. It can also be simply made of a plastic material of the Delrin (i.e., a linear polyoxymethylene-type acetal resin) type or of carbon fiber, but the most suitable material would appear to be Goretex (foamed polytetrafluoroethylene) since the behavior of this material on contact with blood is well-known and appreciated for the uniform and not overly vigorous neoendothelialization which confers low thrombogenicity; this being of particular advantage for devices of this type. The two centrally-hinged flaps are preferably made from pericardium or PTFE, which are biocompatible and behave well under pressure.

The flaps can be fixed to the central support in different ways depending on whether the support is arched, straight or made of a double-arched, sawhorse-like structure (i.e., a structure made of two arches linked in the middle and spreading out laterally until they arrive at that point on the inner surface of the ring which represents the final fixed anchorage of the flaps). In a first embodiment, the two flaps can be obtained from a single piece of material suitably cut and subtending the rib or else the flap can be folded over the rib which thus becomes its support; the flap can be fixed in proper operating position by, e.g., suturing or it could also be kept in place by a system of joints or stays, e.g., rods. In a second embodiment there are two separate flaps which are dome-shaped in order to allow their insertion into the concavity of the two arches. The flaps are fixed to the arches and made integral with them by means of two extensions of the internal and external covering material, these being secured by means of sutures.

The shape of the flaps is therefore conditioned in its upper part by the type of fixing method adopted. On the other hand, in its lower part, it must correspond to the lower internal margin of the internal periphery of the ring which must be closed by the flaps. The flaps are fixed above and at the center of the diameter of the ring, below and externally (laterally) to two opposite points, on the circumference of the disposed along a line parallel to the longitudinal axis of the rib. The lines which connect the lower fixing points to the ring and which constitute the hinge line of the flaps form an angle which varies from 44 to 56 degrees.

In fact, smaller angles would cause the prosthesis to be too high, while larger angles could cause inversion of the flaps causing the valve to become inoperative. Thus, the angle not only conditions the height of the prosthesis but also the amount of mechanical stress to which the flaps are subjected; indeed, smaller angles cause less stress to the flaps. The ideal angle of opening should be an optimum compromise between the various possibilities. The competence of the valve is ensured not only by the geometric rigidity of construction but also by the small height of the prosthesis, which represents an additional safety surface for ensuring effectiveness or competence of the flap when shut (also taking into account a certain elasticity of the flap material). The importance of the height of the prosthesis is therefore evident; it must, on the one hand, be ensured that moderation of the valve action is accomplished with its lateral extension, while, on the other hand, it must not be so cumbersome that it would compromise the ventricular cavity.

The most commonly employed conventional mitral bioprostheses typically have a diameter of 31 mm. in order to guarantee competence, and have a height in profile of 21.8 mm., which is undesirably high, although some of these devices can be reduced to 14 mm., with probable compromise of flap function under stress. In contrast thereto, the significant feature of the present invention is that by linking the height of the prosthesis to the angle formed by the flaps at rest, it is possible, with the use of the very same opening and an angle of about 50° (which ensures competence and sufficient tolerance to the stresses encountered), to manufacture prostheses having heights which vary between 7 mm and 13 mm—these are highly competitive when compared with the previously-mentioned conventional valves. Additionally, if the valve is to be mounted in the aortic position where, when closed, it must deal only with the lower diastolic pressure, it can be made with a wider angle, as a result of which a further reduction in the height of the device is possible.

These and other objects and features of the present invention will become apparent from the following detailed description considered in connection with the accompanying drawings, which disclose several embodiments of the invention. It is to be understood that the drawings are to be used for the purpose of illustration only, and not as a definition of the limits of the invention.

In the drawings, wherein similar reference characters denote similar elements throughout the several views.

Figure 2:
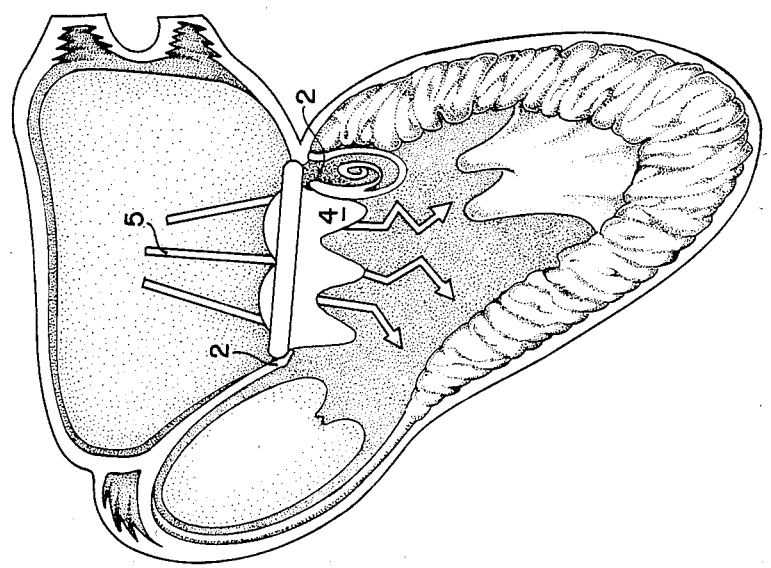
FIG. 2 is a view comparable to that of FIG. 1, but illustrating an implanted, conventional bioprosthesis with arrows depicting relatively poor transprosthetic mitral flow.
Figure 1:
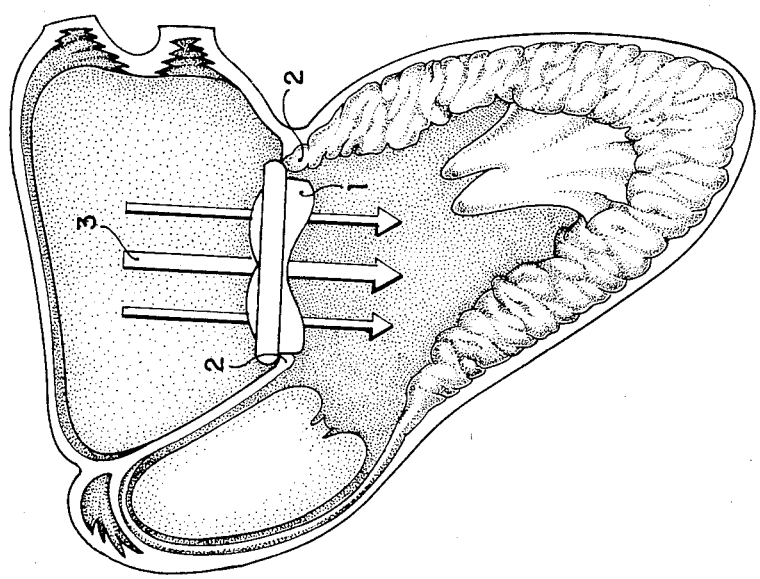
FIG. 1 is a partially schematic side elevational view of the bioprosthesis of the invention implanted in the left ventricle of the heart (shown in section), with arrows depicting the improved transprosthetic mitral flow.
Figure 3:
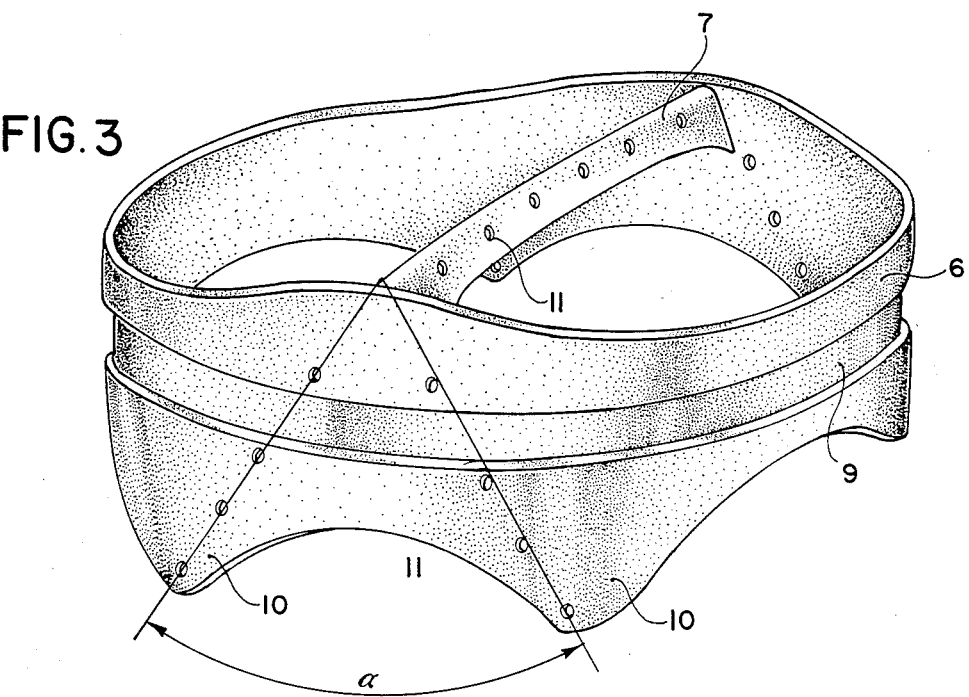
FIG. 3 is a perspective view of one embodiment of the invention prosthesis support structure.
Figure 4:
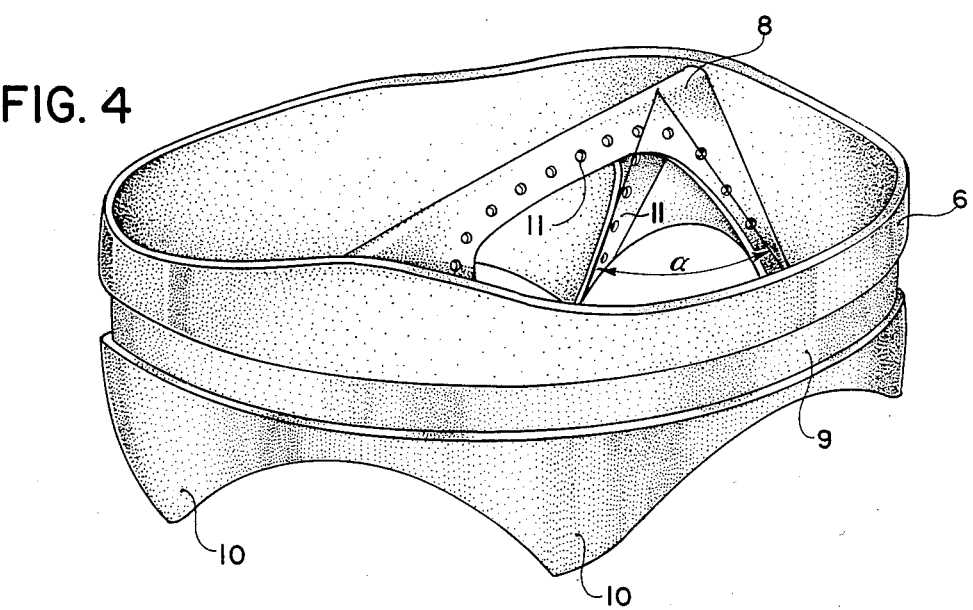
FIG. 4 is a perspective view of a second embodiment of the inventive prosthesis support structure.

Referring now in detail to the drawings, the low profile bioprosthesis embodying the present invention is designated in FIG. 1 by reference numeral 1, the crown for the implant is designated by reference numeral 2 and arrows 3 depict the much improved transprosthetic mitral flow, as compared to the conventional bioprosthesis 4 with long supporting walls shown in FIG. 2 and its corresponding flow 5. The inventive device as shown in FIG. 3 includes a rigid frame, stent or ring 6 and an arched or straight, rigid central rib 7; in the alternative embodiment of FIG. 4, a rib 8 is provided composed of two arches joined together at the center and diverging laterally which assumes a generally sawhorse-like profile. In both embodiments, an annular groove 9 is provided for anchoring the device to the annular crown 2. Each device is also provided with supporting walls 10, and holes 11 for passage of the suture (variously arranged, depending on the embodiment employed) which form an angle α corresponding approximately to that of the valve flaps at rest, which varies between 44 and 56 degrees.

Figure 5:
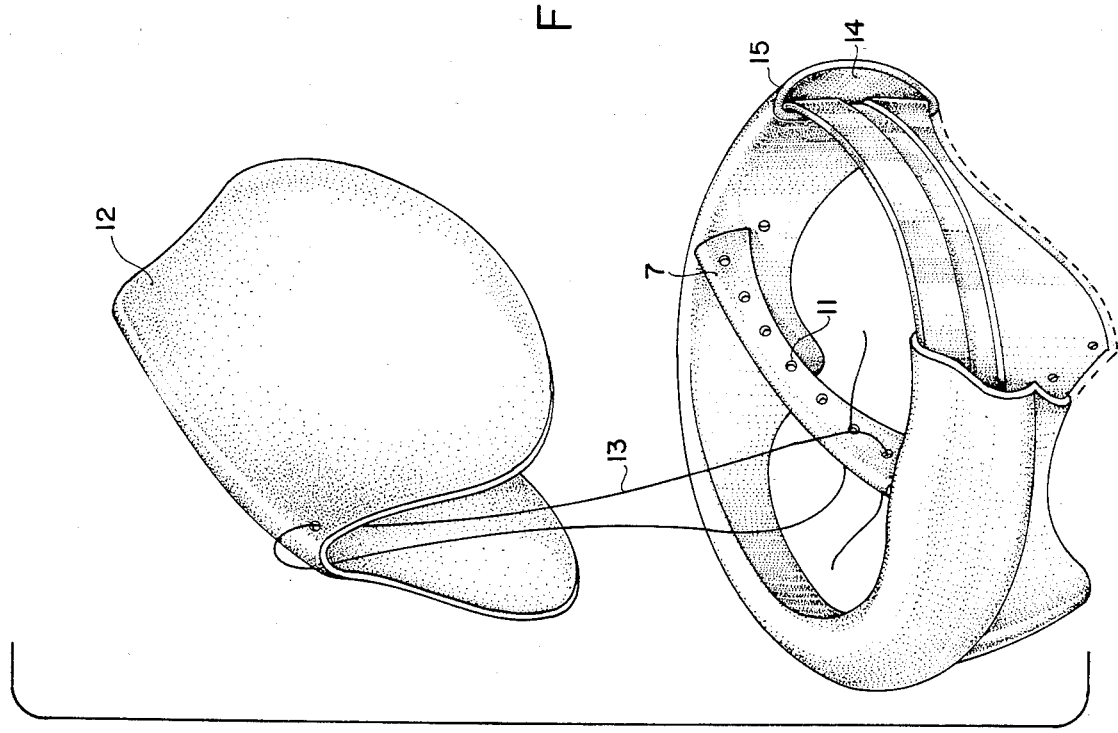
FIG. 5 is a partially-exploded perspective view of a covered prosthesis of the type shown in FIG. 3, with portions broken away to show internal construction and showing one method for mounting the flaps to the curved rib.

FIG. 5 shows the entire flap 12 which, in this embodiment, is mounted on the rib 7 and fixed to it by suturing, with the suture 13 passing through the appropriate holes 11. An annular thickening crown 14, made of suitable plastic material, is also provided which is able to be easily fixed to the implant. A covering 15 or coating of biocompatible material completely covers the bioprosthesis.

Figure 6:
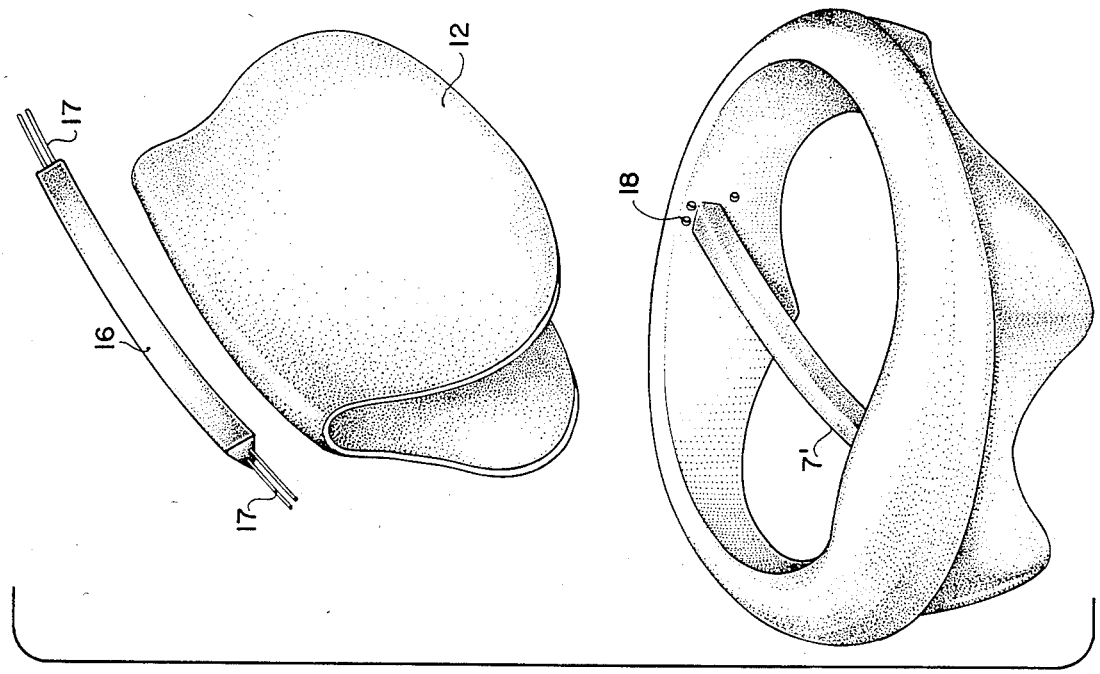
FIG. 6 is a partially exploded perspective view of a covered prosthesis similar to that of FIG. 5, but showing a second method for mounting the flaps to the curved rib.

In the alternate embodiment of FIG. 6, an upper restraining element 16 is provided which cooperates with a modified lower rib 7' to anchor the flap member 12 therebetween; restraining element 16 is provided with anchoring pins 17 which are inserted into complimentary holes 18 of the covering and frame.

Figure 7:
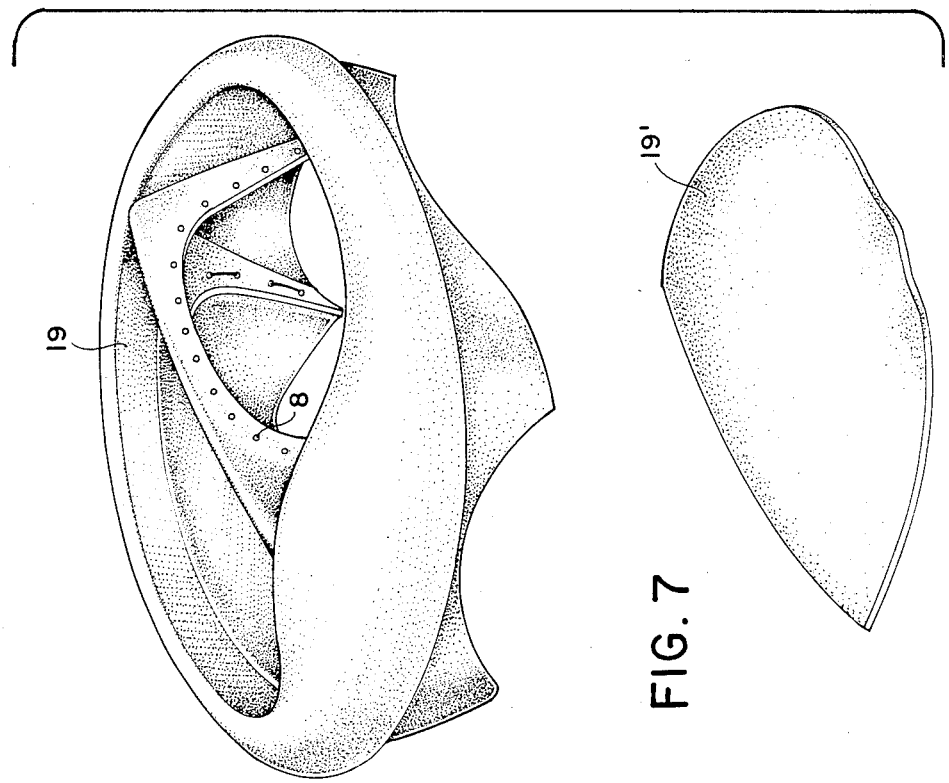
FIG. 7 is a partially exploded perspective view of a covered prosthesis of the type shown in FIG. 4.

In FIG. 7, a dome-shaped flap 19 is mounted in the bioprosthesis, the unmounted dome-shaped flap being represented by numeral 19'.

Figure 8:
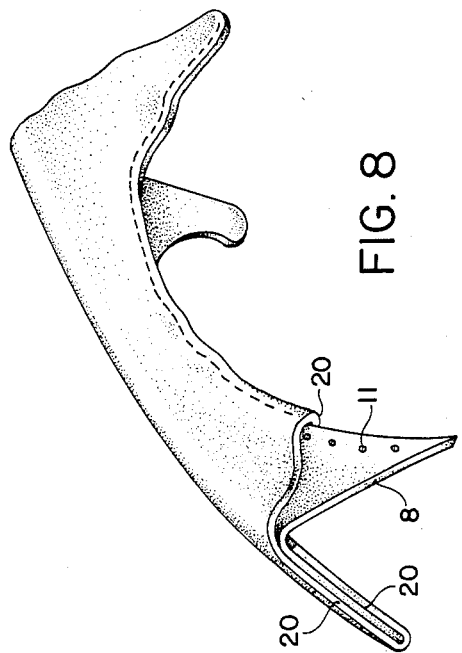
FIG. 8 is a fragmentarily-illustrated perspective view of the covered curved rib of the FIG. 4 embodiment, with portions broken away to show internal construction.
Figure 9:
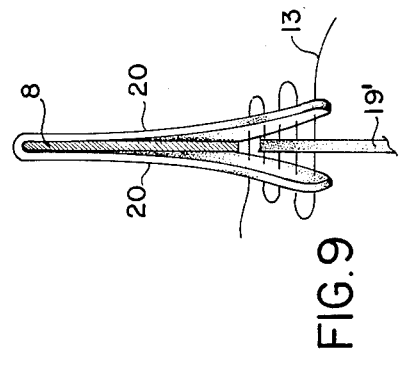
FIG. 9 is a side-elevational view showing the manner of suturing one of the flaps to the covered rib.

As shown in FIGS. 8 and 9, two extensions 20 of the covering material of the central rib element 8 are provided which cover the top edge of the dome-shaped flap once they are sutured together.

While only several embodiments of the present invention have been shown and described, it is obvious that many changes and modifications may be made thereunto, without departing from the spirit and scope of the invention.

What is claimed is:

1. A low-profile biological bicuspid valve prosthesis comprising:
    an annular-like frame having a peripheral external groove disposed around its outside surface;
    an annular-like thickening crown coupled to said frame and engaged with said groove;
    a covering on said crown; and
    a rib centrally disposed within said frame with two flaps fixed to said rib so as to allow movement thereof between an open and closed position relative to said frame, said rib having a generally sawhorse-like configuration and comprising two arched members, each composed of a center base member and two legs depending from opposite ends thereof, which arched members are joined together along their respective center base members with their respective legs diverging laterally outwardly therefrom in a V-like manner, said arched members are secured at both ends to an inner surface of said annular-like frame, said legs each terminating at a point on an inner surface of said frame which represents approximately the lower final point for fixing said flaps to said rib.

2. The prosthesis of claim 1, wherein said frame and rib are made from a biocompatible material selected from the group consisting of a linear polyoxymethylene-type acetal resin, carbon fiber or plastic.

3. The prosthesis of claim 2, wherein said plastic material comprises foamed PTFE.

4. The prosthesis of claim 1, wherein said rib comprises a straight rib.

5. The prosthesis of claim 1, wherein said rib comprises an arched rib.

6. The prosthesis of claim 1, wherein said covering comprises a member selected from the group consisting of pericardium, polyester fiber or PTFE.

7. The prosthesis of claim 1, wherein said flaps in said closed position thereof form an angle of between 44° and 56°.

8. The prosthesis of claim 1, wherein said frame has a cylindrical configuration.

9. The prosthesis of claim 1, wherein said frame has a configuration obtained by straightening the two arch members subtended by the four lower points of intersection with the flaps.

10. The prosthesis of claim 1, wherein said flaps are formed from a single piece of material disposed centrally over said rib.

11. The prosthesis of claim 1, wherein said flaps are composed of two separate, dome-shaped elements made integral with said arch members by means of two extensions of the internal and external covering material, these being fixed together by means of sutures.

12. The prosthesis of claim 1, wherein said flaps are made of a biocompatible material.

13. The prosthesis of claim 12, wherein said biocompatible material is pericardium.

14. The prosthesis of claim 12, wherein said biocompatible material is PTFE.

* * * * *